United States Patent
Rudolph

Patent Number: 5,152,096
Date of Patent: Oct. 6, 1992

[54] BAIT STATION

[75] Inventor: Robin R. Rudolph, Grain Prairie, Tex.

[73] Assignee: Sandoz Ltd., Basel, Switzerland

[21] Appl. No.: 808,054

[22] Filed: Dec. 12, 1991

Related U.S. Application Data

[63] Continuation of Ser. No. 713,480, Jun. 11, 1991, abandoned.

[51] Int. Cl.$^5$ ............................................. A01M 1/20
[52] U.S. Cl. .................................... 43/131; 43/124
[58] Field of Search ................. 43/124, 131, 132.1

[56] References Cited

U.S. PATENT DOCUMENTS

| | | | |
|---|---|---|---|
| 3,972,993 | 8/1976 | Kobayashi et al. | 43/124 X |
| 4,793,093 | 12/1988 | Gentile | 43/132.1 |
| 4,999,346 | 3/1991 | Rudolph | 514/120 |
| 5,057,316 | 10/1991 | Gunner et al. | 43/132.1 X |

Primary Examiner—Richard K. Seidel
Assistant Examiner—Patty E. Hong
Attorney, Agent, or Firm—Allen E. Norris

[57] ABSTRACT

A bait station device for the control of ants, especially of Pharaoh's or Sugar Ant.

5 Claims, 1 Drawing Sheet

BAIT STATION

This is a continuation of application Ser. No. 07/713,480, filed Jun. 11, 1991, now abandoned.

The present invention concerns a bait station device for the control of ants, especially of Pharaoh's or Sugar Ant.

Pharaoh's or Sugar ants [Monomorium pharaonis (L)] have become a major pest due to the combination of their propensity for indoor infestation and synanthropic existence as well as an ability to survive pest control techniques.

They tend to infest areas kept permanently heated such as food stores, households, hospitals and the like with the potential for causing health and sanitary problems due to their apparent ability to act as vectors for infectious agents and thus spread disease. The use of classic insect toxin formulations has proven inadequate to control these ants. This is due to a variety of reasons based on the biological and sociological characteristics of these ants. Colonies are usually polygynous, supporting anything up to tens of thousands of queens. The worker ants appear to have the capability to quite quickly recognize toxins both on surfaces and in baits and avoid them. Workers will often pick up eggs, larvae, pupae and the like and move them to an unaffected area and set up a new colony. Additionally, the fact that few foragers are actually killed and the high level of other survival factors such as high reproduction rate, frequent colony division, low intercolony antagonism, etc., contribute to the problem.

Many attempts have been made to effectively control pharaoh ants, for example employing substances toxic to the ants. These methods although having initial success suffer from a return of ant infestation a few weeks following treatment. Improvements by employing highly attractive baits whilst showing increased success nevertheless require repeat treatments and constant vigilance.

In trying to overcome this problem attempts were made to control pharaoh ants using insect growth regulators (IGRs) such as methoprene. Whilst these products are successful in achieving full and lasting control it may take up to 20 weeks for this control to manifest itself requiring additional quick knock down treatments with toxins (insecticides) for initial control. Each of these methods are costly in terms of material used, labor intensive (repeat treatments) and complicated.

Examples of literature describing such previous attempts include: Burden et.al., J. Med. Ent., 12/3, pp 352–3 (1975); Hrdy et.al and Edwards, International Congress of the International Union for the Study of Social Insects, Wageningen, The Netherlands, 1977; Newton, Int. Pest Control, Sep./Oct. 1980, pp 112–114; Edwards et. al., Regulation of Insect Development and Behavior, Warsaw, Poland, pp 769–778. 1981; Wilson et.al., Pest Control, Mar. 1981, pp 14–16; Rupes et.al., J. Hyg. Epidem. Microb. Immun., 27/3, pp 295–303 (1983)., Granovsky, Pest Management, May 1983, pp 11–16; Granovsky et.al., Pest Control Technology, Mar. 1983, pp 30–34. Products previously recommended against Pharaoh ants include MAXFORCE ® (a.i. hydramethylnon), PHARORID ® (a.i. methoprene).

It has now surprisingly been found according to the present invention that effective, long lasting control without rebounding infestation can be achieved by presenting the ants with a combination of an insect growth regulant (IGR) bait and insecticide bait in such a way that the worker ants have to forage their way through the IGR bait to reach the insecticide bait.

In this way foraging worker ants will transport back to nests for feeding of the colony IGR bait and upon exhausting the available IGR bait will themselves ingest the insecticide bait causing their rapid mortality following contamination of the colony with IGR bait. In this manner initial exposure would be only to IGR allowing queen a broad exposure and ultimately decimation of the colony followed by secondary exposure to insecticide leading to rapid death of worker ants thus preventing them carrying out the normal defense measures.

The invention therefore concerns a pesticidal device which comprises a housing containing an insecticidal bait and an insect growth regulant bait and having therein at least one opening whereby said insecticidal bait is so disposed within said housing that it may only be reached from said opening by removing or passing through said insect growth regulator bait. The devices according to the invention thus provide ready to use control measures for one-off treatment.

It will readily be appreciated that such a device will be suitable for combatting ants of any species however, it is particularly suited for combating pharaoh ants.

The precise nature of the insecticide, IGR and bait is not critical to the functioning of the device.

Thus suitable insecticides are those which are known to be effective on ants. Examples of such insecticides or toxins include boric acid, diazinon, bendiocarb, hydramethylnon, or mixtures of suitable insecticides such as these.

Suitable IGRs include those known to affect the development and growth of insects especially ants and in particular to prevent their survival. Examples include, methoprene, hydroprene, kinoprene, fenoxycarb, or mixtures of suitable IGRs such as these.

Baits suitable for use in preparation of insecticide- and IGR-baits are those conventionally used in ant baits, for example e.g. peanut butter, fishmeal, honey, sugar, mint apple jelly, strained egg yolk, liver, sponge cake, etc. or mixtures thereof. Such baits may also contain attractants such as trail pheromones, quene pheromones, neocembrene-pharoes ant, fire ant pheromones,(E)-6-(1-pentenyl)-2H-pyran-2-one, tetrahydro-3,5-dimethylbutyl-2H-pyran-2-one, and dihydroactindiolide.

Bait material is mixed separately with IGR and insecticide whereby different baits may be used for the two types of active ingredient. For example, it may be desirable to employ a slightly more attractant bait for the insecticide to increase the incentive for the worker ants to work their way through the IGR bait. Baits are preferably not intermingled but are preferably disposed in contact with each other in the device.

Further examples of suitable insecticide, IGRs and baits are contained in the references listed above the contents of which in this respect are incorporated by reference.

The precise nature of the housing is also not essential to the invention provided that it is so arranged as to allow the insecticide bait to be placed in such a manner as to be reachable only through or by removal of the IGR bait.

Thus truncated cylindrical housings such as those used in commercially available devices having a series of substantially axially orientated passages leading from the outer circumference of the cylinder to the center may be employed whereby the insecticide bait is placed at the center of the housing and the IGR bait used to fill the axial entry passages.

Alternatively and preferably tubular housings may be used which may be opened at one end and closed at the other whereby insecticide bait is filled in first to the closed end of the tube followed by IGR bait to close off access to the insecticide bait. The tube may also be open at both ends and contain insecticide bait surrounded on both ends by IGR bait.

When referring to the devices according to the invention as having at least one opening it will be readily appreciated that such openings may be sealed until immediately prior to putting the device to use in order to preserve the integrity and stability of the bait and that such devices with sealed openings are intended to be encompassed by the invention.

The housing may be made from any materials which are convention for such devices. The material will be chosen so as to be compatible with the insecticide and IGR to be employed and be of such thickness and consistency as to prevent loss of active ingredient, and other bait substituents and to prevent absorption and/or loss of moisture from the bait composition. Examples of such materials include e.g. polyvinylchloride, polyethylene terephthalate, high- and low-density polyethylene, polypropylene, glass and the like. Tubes can for example be similar to those used for the imbibing of soft drinks and constructed from heatsealable plastic material such as low-density polyethylene. Other suitable materials will be evident to those skilled in the art.

The size of the device is not critical and will usually be dictated by convenience of packaging and handling and will be large enough to contain sufficient bait but sufficiently small to allow easy concealment. A cylindrical device such as described above and below would conveniently be of diameter between 3 and 6 cms. A tubular device would for example have a diameter of e.g. 3 to 7 mm and a length of 6 to 18 cms depending on amount of bait/a.i. required.

Such devices can be used in any area where control of ants, especially pharaoh and in desired e.g. single and multi-family dwellings, restaurants, zoos, nursing homes, pet shops, etc.

They may simply be placed on the ground or on counter-tops in the relevant areas or conveniently fixed to the underside of surfaces such as counter-tops, tables, widow-sills and the like using for example a strip of two-sided adhesive tape which may be pre-attached to the packaged stations.

The number and placing of the devices will depend upon the size and layout of the area to be treated and the efficacy of the a.i.'s employed and will lie within the experience of the man skilled in the art. For example, the total number of bait stations may vary from 25 for 0–100 ants monitored/2500 sq. ft. to 200 for 500–1000 ants/5000 sq. ft.

A specific embodiment according to the invention will be described below.

Figure 1:
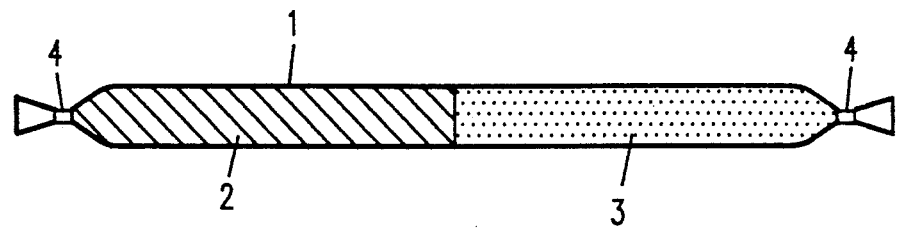
FIG. 1 shows a longitudinal cross-sectional side elevation of a device according to the invention prior to use.
Figure 2:
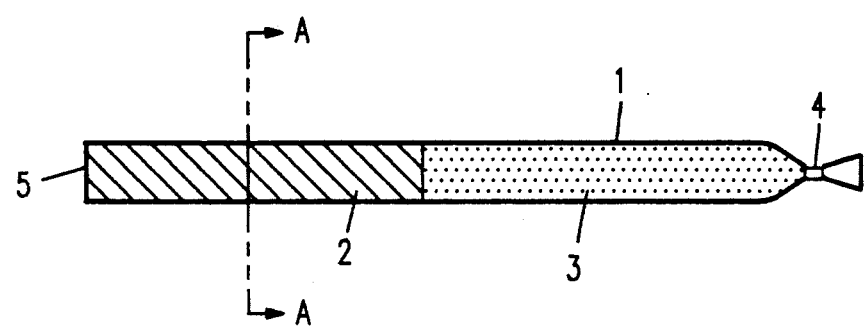
FIG. 2 shows the same view as FIG. 1 with one end of the device opened for use.
Figure 3:
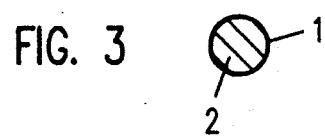
FIG. 3 shows a cross section at A—A of FIG. 2.

The device comprises a hollow tube 1 which may be made of plastic material and preferably clear thermoplastic material such as a drinking straw-like tube. Into this tube 1 is filled in the embodiment shown in FIG. 1 insecticide bait 3 followed by IGR bait 2 to enclose the insecticide bait for example by injection. (Examples of suitable bait composition are given hereinafter.) Following introduction of the bait compositions the tube is sealed at each end 4 for example by heat sealing. In this form the device may be stored until ready for use.

In use the end 5 of the tube 1 which is proximal to the IGR-bait 2 is cut open to expose the bait. Foraging ants attracted by the bait will enter the tube and collect IGR bait which they take back to the nest thus exposing queens and brood. Upon exhaustion of IGR-bait workers collect and ingest insecticide bait causing rapid mortality.

Figure 4:
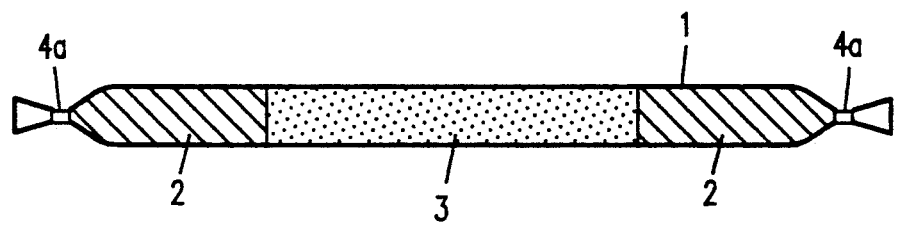
FIG. 4 shows a longitudinal, cross-sectional side elevation of an alternative device according to the invention prior to use.
Figure 5:
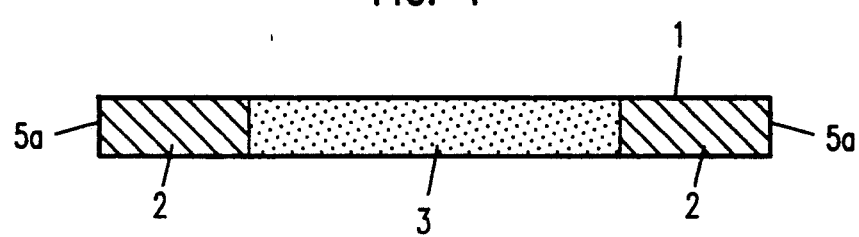
FIG. 5 shows the same view as FIG. 4 with both ends of the device opened for use.

The alternative arrangement shown in FIG. 4 differs from the specific embodiment above in that the insecticide bait 3 is placed in the middle of the tube and is followed by IGR-bait 2 at each end to enclose the insecticide bait 3. The ends 4a are then sealed as described above. In use both ends 5a of the tube are cut open to allow access to the IGR bait.

The following examples further illustrate the invention without in any way restricting its scope.

EXAMPLE 1 (Bait Formulations)

| | | W/W % |
|---|---|---|
| i) | IGR Bait Ingredient | |
| | PHARORID (10% R,S-Methoprene) | 4.8% (0.48% R,S-Methoprene) |
| | Peanut Butter, Creamy | 47.6% |
| | Honey | 47.6% |
| | | 100.0% |
| | Insecticide bait Ingredient | |
| ii)a) | Boric Acid (100% boric acid) | 4.5% |
| | Peanut butter, Creamy | 51.0% |
| | Honey | 38.2% |
| | Water | 6.3% |
| | | 100.0% |
| b) | Boric Acid (100% boric acid) | 4.5% |
| | Peanut butter, Creamy | 44.6% |
| | Honey | 44.6% |
| | Water | 6.3% |
| | | 100.0% |

EXAMPLE 2 (Efficacy)

Field Trial

The trial is carried out in single family homes with existing Pharaoh Ant infestation.

Materials

The test devices are straws with both boric acid and methoprene. These were prepared by placing (via syringe) one gm of boric acid bait (Ex. 1 ii)b)) in the center of each straw, then with a second syringe 0.5 gm of methoprene bait (Ex. 1 i)) at each end of the straw touching the boric acid bait. The ends of each straw are then sealed to be opened at time of treatment.

Population Monitoring

The ant population is monitored before treatment by counting the ants around peanut butter placements. Each placement is ca one gm peanut butter in a plastic weigh boat. (1.75 in square.) These are placed in the immediate area of ant activity. The recommended placement is five stations in kitchen, two stations in each bathroom, and one station in each of the other rooms. The monitoring stations are left overnight and counts of the ants present on and around each station recorded.

This monitoring is done twice pre-treatment and once/week post treatment until ant activity ceases or until four months post treatment. The locations of the monitoring sites are marked and numbered. During treatment, one to four (based on number of ants) of the bait stations are opened and placed at each marked monitoring site, and the weekly post treatment ant counts are made around these. The bait stations in the marked monitoring sites are used post treatment instead of the trays with peanut butter.

TREATMENT

The total number of bait stations for treatment is based on the number of ants counted in the pretreatment survey. The following guidelines are used.

| | GUIDE FOR DETERMINING NUMBER OF BAIT STATIONS | | |
|---|---|---|---|
| | Total No. Ants | Structure Sq. Ft. 2500 | 5000 |
| Pretreatment | 0–100 | 25 | 50 |
| | 100–500 | 50 | 100 |
| Counts | 500–1000 | 100 | 200 |

The majority of the bait stations are placed in areas having the most ant activity. A few stations are placed in each room of the house. Several stations are put around each source of water within the structure.

RESULTS

The results of the above tests at three locations are shown in Table 1.

TABLE 1

| Location | | Weeks Post Treatment | | | | | | | | | | | |
|---|---|---|---|---|---|---|---|---|---|---|---|---|---|
| | | 2 | 3 | 4 | 6 | 7 | 8 | 9 | 11 | 13 | 15 | 17 | 18 |
| (1) | Total Number Ants Pretreat Total = 72 | 92 | 151 | 28 | 19 | 0 | 0 | 0 | 0 | 0 | 0 | 0 | 0 |
| | Percent Reduction | (28) | (110) | 66 | 47 | 100 | 100 | 100 | 100 | 100 | 100 | 100 | 100 |
| | | 1 | 2 | 3 | 5 | 7 | 9 | 11 | 11 | 13 | 15 | 17 | 18 |
| (2) | Total Number Ants Pretreat Total = 691 | 156 | 126 | 75 | 0 | 0 | 6 | 0 | 0 | 0 | 0 | 0 | 0 |
| | Percent Reduction | 77 | 82 | 89 | 100 | 100 | 99 | 100 | 100 | 100 | 100 | 100 | 100 |
| | | 1 | 2 | 3 | 5 | 7 | 9 | 11 | 11 | 13 | 15 | 17 | 18 |
| (3) | Total Number Ants Pretreat Total = 691 | 220 | | 1 | 0 | 0 | 3 | 0 | 0 | 0 | 0 | 0 | 0 |
| | Percent Reduction | 54 | | 100 | 100 | 100 | 99 | 100 | 100 | 100 | 100 | 100 | 100 |

CONCLUSION

As can be seen from the results total control of ant infiltration within 5 to 7 weeks without subsequent rebound activity which indicates destruction of the colony.

We claim:

1. A pesticidal device which comprises a housing containing an insecticidal bait and an insect growth regulant bait and having therein at least one opening whereby said insecticidal bait is so disposed within said housing that it may only be reached from said opening by removing or passing through said insect growth regulator bait.

2. A device according to claim 1 wherein the insecticidal bait and the insect growth regulant bait are in contact with each other but not intermingled.

3. A device according to claim 1 wherein the housing is tubular.

4. A device according to claim 1 wherein the insecticide is boric acid, diazinon, bendiocarb, hydramethylnon, or mixtures thereof.

5. A device according to claim 1 wherein the insect growth regulator is methoprene, hydroprene, kinoprene, fenoxycarb, or mixtures thereof.

* * * * *